United States Patent [19]

Kanter et al.

[11] Patent Number: 4,897,478

[45] Date of Patent: Jan. 30, 1990

[54] PREPARATION OF HALOISATOIC ANHYDRIDES

[75] Inventors: Hartmut Kanter, Ludwigshafen; Heinrich Kowarsch, Oberderfingen; Burkhard Ort, Wachenheim, all of Fed. Rep. of Germany

[73] Assignee: BASF Aktiengesellschaft, Ludwigshafen, Fed. Rep. of Germany

[21] Appl. No.: 239,654

[22] Filed: Sep. 2, 1988

[30] Foreign Application Priority Data

Sep. 11, 1987 [DE] Fed. Rep. of Germany ....... 3730539

[51] Int. Cl.$^4$ ........................................... C07D 265/26
[52] U.S. Cl. ..................................................... 544/94
[58] Field of Search ......................................... 544/94

[56] References Cited

U.S. PATENT DOCUMENTS 4,306,074 12/1981 Tonne et al. ........................... 560/47
4,316,020 2/1982 Reissenweber ....................... 544/105
4,328,339 5/1982 Kilpper et al. ......................... 544/94

FOREIGN PATENT DOCUMENTS 2206863 8/1973 Fed. Rep. of Germany .

OTHER PUBLICATIONS

Chemical Abstracts, Band 100, No. 25, 18. Jun. 1984, Columbus, Ohio, USA Suesse, M.; Johne S. "Quinazolinecarboxylic acids. 2. Quinazolin-4-on-2-ylacetaimdes" Seite 589, Spalte 1, Ausammen.-fassung-Nr. 209 731s & Z. Chem. 1983,23 (11), 406–407.
Chemical Abstracts, Band 101, No. 7, 13 Aug. 1984, Columbus, Ohio, USA Suesse, M.; Johne, S. "Quinazolinecarbozylic acids. I. Quinazolin-4-one(2-,4-dione)-3-acetic acids and esters" Seite 619, Spalte 1, Zusammenfassung-Nr. 55 043a & J. Prakt. Chem. 1984, 326 (2).

Primary Examiner—Richard L. Raymond
Attorney, Agent, or Firm—Oblon, Spivak, McClelland, Maier & Neustadt

[57] ABSTRACT

Haloisatoic anhydrides are prepared by halogenating appropriately unsubstituted isatoic anhydrides with elemental chlorine or bromine in the presence of chlorosulfonic acid at from $-10°$ C. to $+100°$ C. using not less than 0.5 mole of halogen per mole of isatoic anhydride.

5 Claims, No Drawings

PREPARATION OF HALOISATOIC ANHYDRIDES

The present invention relates to a novel process for preparing haloisatoic anhydrides by reacting appropriately unsubstituted isatoic anhydrides with elemental chlorine or bromine in the presence of chlorosulfonic acid.

DE-A-No. 2,206,863 discloses the preparation of 6-chloroisatoic anhydride by reacting isatoic anhydride with sulfuryl chloride. The disadvantage with this method is the presence of inert organic solvents, which substantially cuts the space-time yield.

It is an object of the present invention to provide a new process whereby the preparation of haloisatoic anhydrides is possible in an advantageous manner in a good space-time yield and without recourse to exceptional technical resources.

We have found that this object is achieved with a process for preparing a haloisatoic anhydride of the formula I

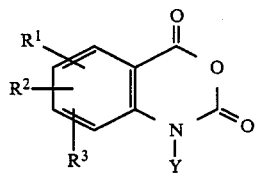

where
Y is hydrogen or $C_1$-$C_4$-alkyl and $R^1$, $R^2$ and $R^3$ are identical or different and each is independently of the others hydrogen, chlorine, bromine, nitro, $C_1$-$C_4$-alkoxy, $C_1$-$C_4$-alkyl, trifluoromethyl, $C_1$-$C_4$-alkanoylamino, carbamoyl, $C_1$-$C_4$-monoalkyl- or -dialkyl-carbamoyl, sulfamoyl or $C_1$-$C_4$-monoalkyl- or -dialkyl-sulfamoyl, with the proviso that at least one of the radicals $R^1$, $R^2$ or $R^3$ is chlorine or bromine, by halogenating an isatoic anhydride of the abovementioned formula I where Y, $R^1$, $R^2$ and $R^3$ are each as defined above and at least one of the radicals $R^1$, $R^2$ or $R^3$ is hydrogen with elemental chlorine or bromine in the presence of chlorosulfonic acid at from $-10°$ C. to $+100°$ C. using not less than 0.5 mole of halogen per mole of isatoic anhydride.

All the alkyls appearing in the abovementioned formula I may be not only straight-chain but also branched.

$R^1$, $R^2$ and $R^3$ and Y of the formula I are each for example methyl, ethyl, propyl, isopropyl, butyl, isobutyl or sec-butyl.

$R^1$, $R^2$ and $R^3$ are each further for example methoxy, ethoxy, propoxy, isopropoxy, butoxy, isobutoxy, sec-butoxy, formylamino, acetylamino, propionylamino, butyrylamino, isobutyrylamino, monomethylcarbamoyl, dimethylcarbamoyl, monoethylcarbamoyl, diethylcarbamoyl, monopropylcarbamoyl, dipropylcarbamoyl, monoisopropylcarbamoyl, diisopropylcarbamoyl, monobutylcarbamoyl, dibutylcarbamoyl, N-methyl-N-ethylcarbamoyl, monomethylsulfamoyl, dimethylsulfamoyl, monoethylsulfamoyl, diethylsulfamoyl, monopropylsulfamoyl, dipropylsulfamoyl, monobutylsulfamoyl, dibutylsulfamoyl or N-methyl-N-ethylsulfamoyl.

Preferably, Y is hydrogen or methyl and $R^1$, $R^2$ and $R^3$ are each hydrogen, chlorine, bromine or nitro.

Starting from a ring-unsubstituted isatoic anhydride of the formula II

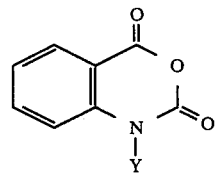

where Y is as defined above, the process according to the invention makes possible the preparation not only of mono- but also of di- and trihaloisatoic anhydrides.

If the halogenation is carried out with chlorine and bromine in succession in either order, the products obtained are haloisatoic anhydrides containing not only chlorine but also bromine in the aromatic ring.

According to the invention, not less than 0.5 mole of halogen (chlorine or bromine) is to be used per mole of isatoic anhydride I.

If a monohalogenation is carried out, the amount used per mole of isatoic anhydride I is preferably from 0.5 to 1.5 moles of halogen. For di- or trihalogenations, these amounts must be doubled or tripled, as appropriate.

It is also possible to start from previously halogenated isatoic anhydride, in which case it is then possible to introduce a further one or two chlorine and/or bromine atoms into the aromatic ring.

Preferably, the novel process is carried out in the presence of a catalyst. The catalyst used is iodine or a compound which liberates iodine under the reaction conditions.

Such compounds are for example iodohydric acid, alkali metal iodides, such as sodium iodide and potassium iodide, alkali metal iodates, such as sodium iodate and potassium iodate, and alkali metal periodates, such as sodium periodate and potassium periodate.

This catalyst is usually added in an amount of from 0.1 to 2% by weight, based on the solvent.

The solvent used in the reaction is chlorosulfonic acid, generally in an amount of from 2 to 10 parts by weight, based on 1 part by weight of isatoic anhydride.

A preferred procedure comprises performing the halogenation in a mixture of chlorosulfonic acid and oleum (from 20 to 70% strength by weight in $SO_3$). This is of importance in particular if the target products are isatoic anhydrides having two or three chlorine and/or bromine atoms in the aromatic ring.

It has proved particularly advantageous in this connection to add to the chlorosulfonic acid from 0.1 to 2 parts by weight of oleum, based on one part by weight of isatoic anhydride I.

According to the invention, the halogenation is carried out at from $-10°$ C. to $+100°$ C., preferably at from $0°$ to $+50°$ C.

In general, the novel process is carried out under atmospheric pressure. In some cases, however, it may be of advantage to employ a small superatmospheric pressure (up to 1.5 bar).

The process according to the invention is advantageously implemented by initially introducing chlorosulfonic acid, with or without oleum, and adding the isatoic anhydride with or without a catalyst with stirring at from $-10°$ to $+50°$ C., preferably at from $0°$ to $+20°$ C. The particular halogen is then added at the stated temperature, and the temperature is raised, if desired.

After stirring for from 1 to 10 hours the reaction has ended. The reaction mixture is then cooled down if necessary and discharged onto from 5 to 20 parts by weight of water, based on one part of chlorosulfonic acid, and the product precipitates.

For the precipitating step the temperature should be at from 0° to 30° C. This is obtained by external cooling or by precipitating in ice-water.

The haloisatoic anhydride is then separated off, washed and dried.

The novel process can be carried out not only continuously but also batchwise.

The advantages of the process according to the invention reside in its universal applicability. High space-time yields are obtained, the halogenation proceeding in high selectivity and without ring opening. Furthermore, no organic solvent is present.

The haloisatoic anhydrides of the formula I obtained by means of the process according to the invention are useful intermediates for dyes, pigments and crop protection agents.

The Examples which follow serve to illustrate the invention in more detail.

EXAMPLE 1

60 g of isatoic anhydride were added at room temperature to 100 g of chlorosulfonic acid. After the addition of 2 g of potassium iodide, 30 g of bromine were added dropwise in the course of 3 hours and subsequently stirred in for 10 hours under nitrogen. The reaction mixture was then poured slowly into 1,200 g of an ice-/water mixture without the temperature being allowed to rise above 10° C., and the precipitated product was filtered off with suction. The filter residue was washed with a little cold water and dried at 100° C. to leave 75 g of a colorless powder (bromine value 34.1%, theory 33.1%) of the formula

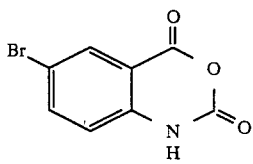

EXAMPLE 2

65 g of isatoic anhydride were added at room temperature to 120 g of chlorosulfonic acid. After the addition of 2 g of potassium iodide, 48 g of bromine were added dropwise in the course of 2.5 hours and stirred in for 1 hour. 47 g of oleum (65% strength) were then added in the course of 1 hour, a further 32 g of bromine were added dropwise at room temperature in the course of 3 hours, and thereafter the reaction mixture was stirred for 2 hours. The reaction mixture was then slowly poured into 1,200 g of ice/water mixture while the temperature was not allowed to rise above 10° C., and the precipitated product was filtered off with suction. The filter residue was washed with a little cold water and dried at 100° C. to leave 128 g of a light-colored powder (bromine value 49.6%, theory 49.8%) of the formula

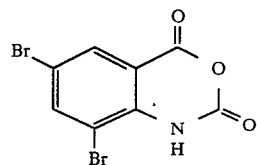

EXAMPLE 3

70 g of isatoic anhydride and 2 g of potassium iodide were added at from 15° to 20° C. to 200 g of chlorosulfonic acid. 40 g of chlorine gas were then passed in at 20° C. in the course of 6 hours. After the addition of 120 g of oleum (65% strength) at from 15° to 20° C. a further 100 g of chlorine gas were passed in at from 45° C. to 50° C. in the course of 6 hours, and the solution was then stirred at that temperature for 2 hours. The solution was cooled down to room temperature and then poured onto 1,200 g of ice-water. The temperature was maintained below 10° C. by adding ice. The mixture was filtered cold, and the filter residue was washed neutral and dried to leave 90 g of colorless powder (chlorine value 39.4%, theory 39.9%) of the formula

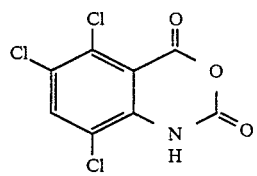

EXAMPLE 4

320 g of isatoic anhydride and 10 g of crystalline potassium iodide were added at from 5 to 10° C. to 1,000 g of chlorosulfonic acid. 170 g of chlorine gas were then passed in at from 15° to 20° C. in the course of 3 hours. After one hour of stirring 260 g of oleum (65% strength) were added. 170 g of bromine were then added dropwise at from 15° to 20° C. in the course of 3 hours. After all the bromine had been added, the mixture was heated at from 35° to 40° C. for 2 hours. After cooling down to room temperature, the solution was discharged onto a mixture of 5,000 g of ice and 2,000 ml of water, and the temperature was maintained at 0° C. by the addition of a further 3,000 g of ice. The mixture was filtered cold, and the filter residue was washed neutral with cold water and dried to leave 460 g of a colorless powder (chlorine value 12.4%, theory 12.8%; bromine value 29.3%, theory 28.9%) of the formula

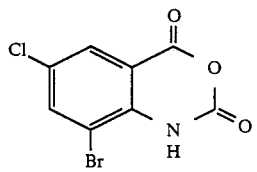

EXAMPLE 5

120 g of 4-chloroisatoic anhydride and 2 g of potassium iodide were added to 440 g of chlorosulfonic acid. 210 g of bromine were added dropwise at room temperature in the course of 30 minutes. The reaction mixture was then stirred for 5 hours, heated to 50° C. and stirred for a further 5 hours. After cooling down, the reaction mixture was poured onto 2,000 g of ice/water mixture, and the precipitated product was filtered off with suction and dried to leave 210 g of a light-colored powder (chlorine value 9.7%, theory 10.0%; bromine value 45.2%, theory 45.0%) of the formula

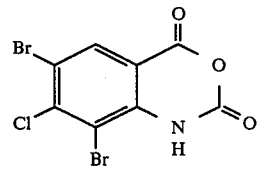

The following Examples were carried out in a similar manner:

| Example No. | Reaction scheme |
|---|---|
| 6 | |
| 7 | |
| 8 | |
| 9 | |
| 10 | |
| 11 | |
| 12 | |

| Example No. | Reaction scheme |
|---|---|
| 13 | 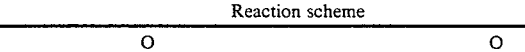 |

We claim:
1. A process for preparing a haloisatoic anhydride of the formula I

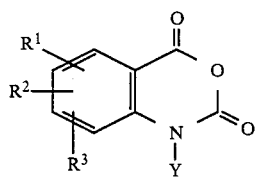

where
Y is hydrogen or $C_1$–$C_4$-alkyl and
$R^1$, $R^2$ and $R^3$ are identical or different and each is independently of the others hydrogen, chlorine, bromine, nitro, $C_1$–$C_4$-alkoxy, $C_1$–$C_4$-alkyl, trifluoromethyl, $C_1$–$C_4$-alkanoylamino, carbamoyl, $C_1$–$C_4$-monoalkyl- or -dialkyl-carbamoyl, sulfamoyl or $C_1$–$C_4$-monoalkyl- or -dialkyl-sulfamoyl, with the proviso that at least one of the radicals $R^1$, $R^2$ or $R^3$ is chlorine or bromine, comprising halogenating an isatoic anhydride of the abovementioned formula I where Y, $R^1$, $R^2$ and $R^3$ are each as defined above and at least one of the radicals $R^1$, $R^2$ or $R^3$ is hydrogen with elemental chlorine or bromine in the presence of chlorosulfonic acid at from $-10°$ C. to $+100°$ C. using not less than 0.5 mole of halogen per mole of isatoic anhydride.

2. A process as claimed in claim 1, wherein the halogenation is carried out in the presence of iodine, or of a compound which liberates iodine under the reaction conditions, as catalyst.

3. A process as claimed in claim 1, wherein the halogenation is carried out at from $0°$ to $+50°$ C.

4. A process as claimed in claim 1, wherein from 2 to 10 parts by weight of chlorosulfonic acid are used per part by weight of isatoic anhydride.

5. A process as claimed in claim 1, wherein the reaction is carried out in a mixture of chlorosulfonic acid and oleum.

* * * * *